US00PP17635P2

(12) United States Plant Patent
Ghyselen

(10) Patent No.: US PP17,635 P2
(45) Date of Patent: Apr. 24, 2007

(54) ***PERSICARIA* PLANT NAMED 'BLACKFIELD'**

(50) Latin Name: *Persicaria amplexicaulis*
Varietal Denomination: Blackfield

(75) Inventor: Chris Ghyselen, Oedelem (BE)

(73) Assignee: Future Plants Licentie B.V., Lisserbroek (NL)

( * ) Notice: Subject to any disclaimer, the term of this patent is extended or adjusted under 35 U.S.C. 154(b) by 66 days.

(21) Appl. No.: 11/151,834

(22) Filed: Jun. 14, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Persicaria* plant named 'Blackfield', characterized by its upright and outwardly spreading plant habit; dark red-colored flowers; freely and continuous flowering habit; and good garden performance.

2 Drawing Sheets

Botanical designation: *Persicaria amplexicaulis.*
Cultivar denomination: 'Blackfield'.

BACKGROUND OF THE INVENTION

The present Invention relates to a new and distinct cultivar of *Persicaria* plant, botanically known as *Persicaria amplexicaulis,* and hereinafter referred to by the cultivar name Blackfield.

The new *Persicaria* is a product of a planned breeding program conducted by the Inventor in Oedelem (Beernem), Belgium. The objective of the breeding program was to create new *Persicaria* cultivars with attractive flower coloration.

The new *Persicaria* originated from a cross-pollination made by the Inventor in 2001 in Oedelem (Beernem), Belgium of an unnamed selection of *Persicaria amplexicaulis,* not patented, as the female, or seed, parent with an unnamed selection of *Persicaria amplexicaulis,* not patented, as the male, or pollen, parent. The new *Persicaria* was discovered and selected by the Inventor as a flowering plant within the progeny of the stated cross-pollination in a controlled environment in Oedelem (Beernem), Belgium during the summer of 2002.

Asexual reproduction of the new cultivar by cuttings at Oedelem (Beernem), Belgium since 2002, has shown that the unique features of this new *Persicaria* are stable and reproduced true to type in successive generations.

SUMMARY OF THE INVENTION

Plants of the cultivar Blackfield have not been observed under all possible environmental conditions. The phenotype may vary somewhat with variations in environment such as temperature and light level without, however, any variance in genotype.

The following traits have been repeatedly observed and are determined to be the unique characteristics of 'Blackfield'. These characteristics in combination distinguish 'Blackfield' as a new and distinct cultivar of *Persicaria:*

1. Upright and outwardly spreading plant habit.
2. Dark red-colored flowers.
3. Freely and continuous flowering habit.
4. Good garden performance.

Plants of the new *Persicaria* differ primarily from plants of the parent selections in flower color as plants of the parent selections have lighter red-colored flowers. In addition, plants of the new *Persicaria* have more attractive fall coloration than plants of the parent selections.

Plants of the new *Persicaria* can be compared to the *Persicaria amplexicaulis* cultivar Taurus, disclosed in U.S. Plant Pat. No. 9,682. Plants of the new differ from plants of the cultivar Taurus in the following characteristics:

1. Plants of the new *Persicaria* have darker green-colored leaves than plants of the cultivar Taurus.
2. Plants of the new *Persicaria* have darker red-colored flowers than plants of the cultivar Taurus.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Persicaria.*

The photograph on the first sheet comprises a side perspective view of a typical flowering plant of 'Blackfield'.

The photograph at the top of the second sheet is a close-up view of a typical inflorescence of 'Blackfield'.

The photograph at the bottom of the second sheet is a close-up view of the upper surface of a typical leaf of 'Blackfield'.

DETAILED BOTANICAL DESCRIPTION

The aforementioned photographs, following observations and measurements describe plants grown in Lisserbroek, The Netherlands, in an outdoor nursery and under commercial production practices during the summer and fall. Plants were about two years old when the photographs and description were taken. During the production of the plants, day temperatures ranged from 12 to 24° C. and night temperatures ranged from 4 to 12° C. In the following description, color references are made to The Royal Horticultural Society Colour Chart, 2001 Edition, except where general terms of ordinary dictionary significance are used.

Botanical classification: *Persicaria amplexicaulis* cultivar Blackfield.

Parentage:

*Female parent.*—Unnamed selection of *Persicaria amplexicaulis,* not patented.

*Male parent.*—Unnamed selection of *Persicaria amplexicaulis,* not patented.

Propagation:

*Type.*—By cuttings.

*Time to initiate roots.*—About 30 days at 20° C.

*Time to produce a rooted plant.*—About 50 days at 20° C.

*Root description.*—Fibrous; moderately fine; very dark brown to almost black in color.

*Rooting habit.*—Freely branching; dense.

Plant description:

*Plant form/habit.*—Upright and outwardly spreading; broad inverted triangle; moderately vigorous growth habit.

*Plant height.*—About 66 cm.

*Plant width* (*spread*).—About 76 cm.

*Lateral branches.*—Length: About 46 cm. Diameter: About 3 mm. Internode length: About 9.2 cm. Strength: Strong. Texture: Smooth, glabrous. Color: 144A.

*Foliage description.*—Arrangement: Alternate, simple. Length: About 13.1 cm. Width: About 5.5 cm. Shape: Ovate. Apex: Apiculate. Base: Cordate. Margin: Finely and irregularly serrate; undulate. Texture, upper and lower surfaces: Pubescent, scabrous. Venation pattern: Pinnate. Color: Developing leaves, upper surface: Between 137A and 143A. Developing leaves, upper and lower surfaces: 137C to 138A. Fully expanded leaves, upper surface: Between 137B and 146A. Fully expanded leaves, lower surface: 137C to 138A. Venation, upper surface: 148B. Venation, lower surface: 145B to 145C. Petiole length: About 2.5 cm. Petiole diameter: About 3 mm. Petiole color: 145A to 145B.

Flower description:

*Flower type/habit.*—Single rotate flowers arranged in terminal racemes; flowers face outward to slightly upright. Freely flowering habit with about 165 flower buds and flowers per inflorescence.

*Fragrance.*—Faint.

*Natural flowering season.*—Continuously flowering from late August through October in The Netherlands. Flowers not persistent.

*Postproduction longevity.*—Flowers last about one week on the plant.

*Inflorescence height.*—About 7.7 cm.

*Inflorescence diameter.*—About 1.7 cm.

*Flower buds.*—Height: About 5 mm. Diameter: About 2 mm. Shape: Ovate. Color: 59A to 60A.

*Flowers.*—Diameter: About 6 mm. Depth: About 5 mm.

*Petals.*—Quantity per flower: Typically five in a single whorl. Length: About 3 mm. Lobe width: About 2 mm. Shape: Ovate. Apex: Bluntly acute to obtuse. Margin: Entire. Texture, upper and lower surfaces: Smooth, glabrous. Color: When opening and fully opened petals, upper surface: 53B; color becoming closer to 187C to 187D with development. When opening and fully opened petals, lower surface: 53A to 60A.

*Sepals.*—Sepals have not been observed.

*Peduncles.*—Length: About 12.3 cm. Diameter: About 2 mm. Aspect: About 10° from vertical. Strength: Strong. Color: 144A.

*Pedicels.*—Length: About 3 mm. Diameter: About 0.5 mm. Aspect: About 30° from vertical. Strength: Moderately strong. Color: 53A.

*Reproductive organs.*—Stamens: Quantity per flower: Typically seven. Filament length: About 3.5 mm. Filament color: 53B; towards the base, 53C. Anther shape: Elliptic. Anther length: About 0.5 mm. Anther color: 202A. Pollen amount: Scarce. Pollen color: 202D. Pistils: Quantity per flower: Typically three. Pistil length: About 4 mm. Stigma shape: Acute. Stigma color: 53A. Style length: About 3.8 mm. Style color: 53B. Ovary color: 165B.

*Seed/fruit.*—Seed and fruit development have not been observed.

Disease/pest resistance: Plants of the new *Persicaria* have not been noted to be resistant to pathogens and pests common to *Persicaria.*

Garden performance: Plants of the new *Persicaria* have been observed to have good garden performance and tolerate rain, wind, are hardy to USDA Zone 5 and tolerate temperatures as high as 35° C.

It is claimed:

1. A new and distinct cultivar of *Persicaria* plant named 'Blackfield', as illustrated and described.

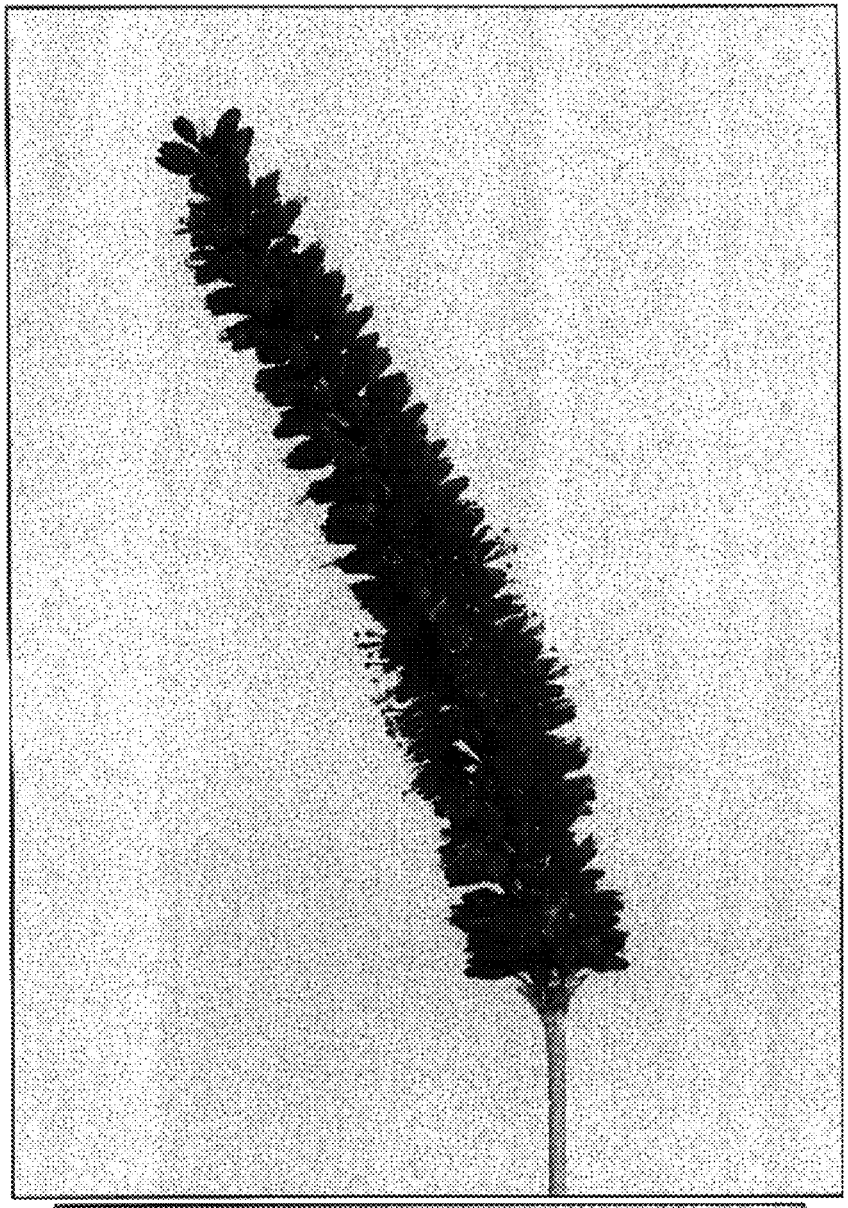
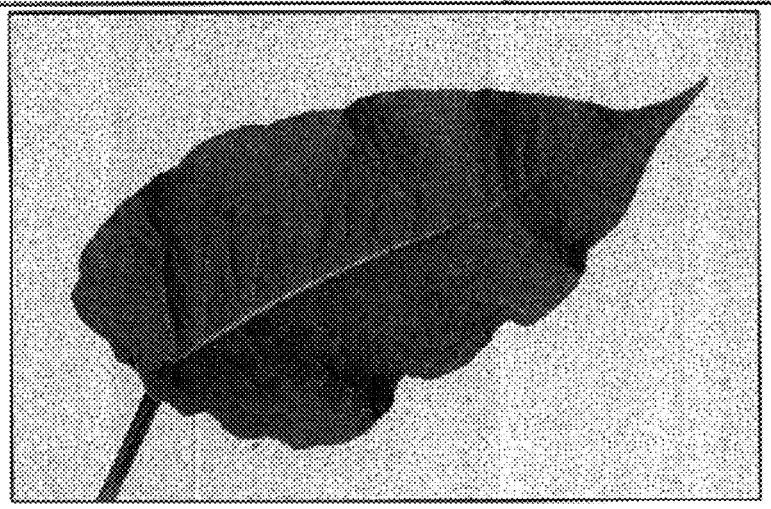

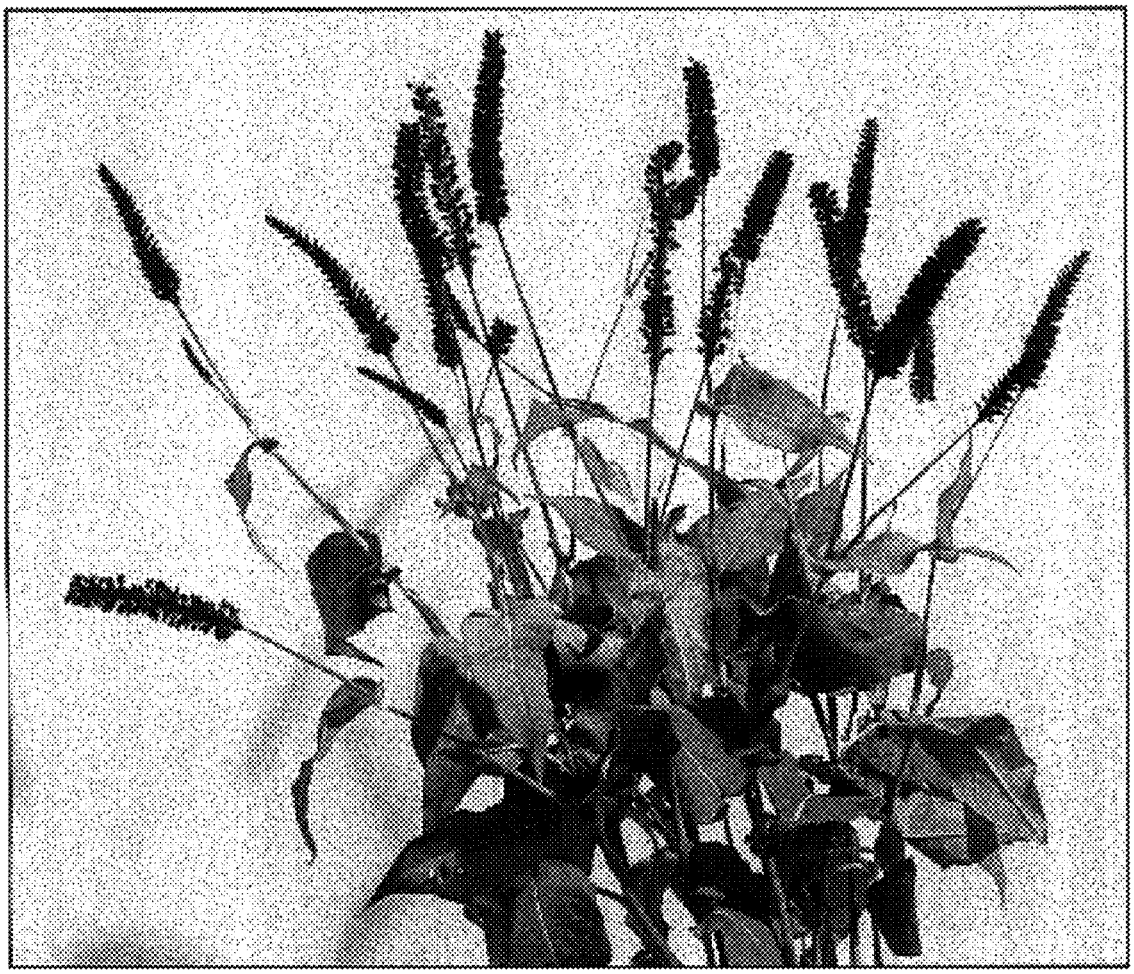

* * * * *